US00PP12627P2

(12) United States Plant Patent
Nelson et al.

(10) Patent No.: US PP12,627 P2
(45) Date of Patent: May 14, 2002

(54) STRAWBERRY PLANT DESIGNATED 'BG-424'

(75) Inventors: Steven D. Nelson; Mike D. Nelson, both of Watsonville; Leo W. Stoeckle, Ventura, all of CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 09/399,952

(22) Filed: Sep. 20, 1999

(51) Int. Cl.[7] ..... A01H 5/00
(52) U.S. Cl. ..... Plt./208

(58) Field of Search ..... Plt./208, 209

*Primary Examiner*—Bruce R. Campell
*Assistant Examiner*—Michelle Kizilkaya
(74) *Attorney, Agent, or Firm*—Foley & Lardner

(57) ABSTRACT

This invention relates to a new and distinct winter planted short day variety of strawberry known as 'BG-424'. This new variety is primarily adapted to the growing conditions of the southern coast of California. It is particularly characterized by its moderate vigor and dense plant. 'BG-424' has a medium to large cylindrical to wedged shaped berry. Seeds are positioned below the surface of the berry with a narrow band without achenes under the calyx. The fruit is medium red in color with good flavor.

2 Drawing Sheets

SUMMARY OF THE INVENTION

The present invention relates to a new and distinct short-day strawberry variety designated as 'BG-424'. This new variety is a result of a controlled cross of 'PS-1879' (an unpatented proprietary selection) and 'Camarosa' (U.S. Plant Pat. No. 8,708). The variety is botanically known as *Fragaria ananassa*.

In comparison to the parental cultivar 'Camarosa', 'BG-424' fruit size is larger, lighter in color, and more vigorous in plant growth. In comparison to parental cultivar 'PS-1879', 'BG-424' has higher fruit yield, and is more vigorous in plant growth. These comparisons are made in a side by side trial grown in Oxnard, Calif.

The seedling resulting from the aforementioned cross was asexually propagated by stolons in a nursery located in Lassen County, Calif., and was subsequently selected from a controlled breeding plot near Oxnard, Calif. in 1996. After its selection, the new variety was further asexually propagated in both Lassen County, Calif. and Siskiyou County, Calif. by stolons and extensively tested over the next several years in fruiting fields near Oxnard, Calif. This propagation has demonstrated that the combination of traits disclosed herein as characterizing the new variety are fixed and remain true to type through successive generations of asexual reproduction.

BRIEF DESCRIPTION OF THE PHOTOGRAPHS

The accompanying color photographs show typical specimens of the new variety at various stages of development as nearly true as it is possible to make in color reproductions:

Photograph 1 shows a close-up view of typical field-fruiting characteristics in mid-April 1999.

Photograph 2 shows a close-up view of fruit harvested in mid-April 1999 and packed in a standard twelve dry pint crate.

DESCRIPTION OF THE NEW VARIETY

'BG-424' is primarily adapted to the climate and growing conditions of the southern coast of California. This region provides the necessary winter temperatures required for it to produce a strong vigorous plant and to remain in fruit production from January through June. The nearby Pacific Ocean provides the needed humidity and moderate temperatures to maintain fruit quality during the winter and spring production months. The following list of traits in combination define 'BG-424' as a unique variety distinguishing it from the most widely grown commercial variety in the region, 'Camarosa' (U.S. Plant Pat. No. 8,708).

'BG-424' is a medium to large moderately vigorous plant. When provided with optimum chilling in the nursery propagation fields prior to being dug and subsequently artificially cold stored prior to being planted, the plant of the new variety is larger and more vigorous than 'Camarosa'. The plant 'BG-424' is also denser in growth habit than 'Camarosa'. The foliage of 'BG-424' is slightly darker in color yet overall similar in size and shape as 'Camarosa'. The upper leaf surface coloration of 'BG-424' is 7.5 GY 3/4 to 7.5 GY 3/6, and the lower surface is nearest to 7.5 GY 5/4 to 7.5 GY 6/4 (Munsell color). 'BG-424' has medium to strong leaf blistering while 'Camarosa' has medium leaf blistering. Petioles of 'BG-424' are longer in length and larger in diameter than the petioles of 'Camarosa'. Table 4 illustrates foliage characteristics of 'BG-424' and 'Camarosa'.

'BG-424' is capable of long season fruit production with fruit of good size good quality during the entire season when provided with optimum chilling in the nursery propagation fields and artificial cold storage prior to being planted. Fruit production begins in late December to early January, up to 7 days earlier than 'Camarosa' and may continue cropping into June. 'BG-424' typically produces fewer runners per plant with a similar average fruit size and generally overall less production than 'Camarosa' (Table 1). The fruit of 'BG-424' is similar in shape and appearance to 'Camarosa'. 'BG-424' has a narrow band without achenes under the calyx while 'Camarosa' has a moderate band. The calyx of 'BG-424' is typically held flat to the surface of the berry while the calyx of 'Camarosa' is positioned reflexed to the berry. The fruit of 'BG-424' has a lighter skin color than 'Camarosa'. The flesh of the fruit of 'BG-424' is very firm while the flesh of the fruit of 'Camarosa' is extremely firm. See Table 3 for fruit quality performance ratings. The pedicel holding the primary berry of 'BG-424' is shorter than the pedicel of 'Camarosa'. See Table 5 for inflorescence characteristics.

For indentification, a series of molecular markers have been determined for this new variety.

SPECIFIC DESCRIPTION OF THE NEW VARIETY

The following is a detailed description of 'BG-424', including the variety's morphological, and pest and disease reaction characteristics. This detailed description is based on observations taken during the 1999 growing season in Oxnard, Calif. These measurements and ratings were made from plants dug from a high-elevation nursery located in Siskiyou County, Calif. in October 1998 and planted 5 later in Oxnard, Calif. The approximate age of the observed plant is 26 weeks for fruit evaluation; 28 weeks for flower evaluation; 29 weeks for foliage evaluation; and 34 weeks for inflorescence evaluation. Yield observations were taken from the 1998–1999 growing season. The characteristics of the new variety may vary in detail, depending upon variations in environmental factors, including weather (temperature, humidity and light intensity), day length, soil type and location without any change in the genotype. 'BG-424' has not been observed under all possible environmental conditions. Color terminology follows the Munsell Book of Colors, Munsell Color, Baltimore, Md. (1976).

Fruit Characteristics

'BG-424' fruit, fruit production and runner production (fruiting field) characteristics as compared to those of 'Camarosa'.

TABLE 1

1998–1999 market fruit yield, fruit size and runner production characteristics from plants harvested from January through June 1, 1998 and 1999 of 'BG-424' dug from a high elevation nursery (Macdoel, California) during the first week of October and planted 4 to 5 days later and compared with 'Camarosa' in Oxnard, California

| Cultivar | 1998 Total Fresh* Yield GM/PL | 1999 Total Fresh* Yield GM/PL | 1998–1999 Average Fresh* Yield GM/PL | 1998–1999 Average Fruit Size Fresh GRM | 1998 Average Runners/ PL |
|---|---|---|---|---|---|
| 'BG-424' | 523 | 946 | 735 | 26.3 | 1.7 |
| 'Camarosa' | 661 | 876 | 768 | 24.9 | 3.1 |

*Fresh fruit harvested from January through June 1

TABLE 2

Comparison of primary fruit characteristics of 'BG-424' and 'Camarosa' from Oxnard, California, April 16, 1999

| Character | 'BG-424' | 'Camarosa' |
|---|---|---|
| Munsell Color | 7.5 R 3/10 to 7.5 R 4/10 | 5 R 3/8 to 5 R 3/10 |
| Primary Fruit Length | | |
| mean (cm) | 5.3 | 5.2 |
| range | 4.4–6.0 | 4.7–5.7 |
| Primary Fruit Width | | |
| mean (cm)* | 4.5 | 4.6 |
| range | 3.8–5.6 | 3.9–5.3 |
| Primary Fruit Ratio (L/W) | 1.18 | 1.13 |
| Calyx Diameter | | |
| mean (cm) | 5.6 | 5.8 |
| range | 4.7–7.3 | 4.7–7.7 |

*Width is measured across the widest part of the berry, typically across the shoulders

TABLE 3

Comparison of 1997–1999 fruit quality characteristics of 'BG-424' and 'Camarosa' from Oxnard, California.*

| Character | 'BG-424' | 'Camarosa' |
|---|---|---|
| Skin Firmness | 8.3 | 8.7 |
| Fruit Appearance | 7.2 | 7.1 |
| Fruit Gloss | 7.6 | 7.5 |

*Results are averaged from 3 years of replicated holding tests performed from January through May 1997–1999. Ratings are based on a scale from 1–10; the higher the rating, the stronger the skin and more attractive and glossy the berry.

The fruit is medium to large in size and characteristically cylindrical to wedged in shape. Berries are typically much greater in length than width as described by the length/width ratio. See Table 2 for fruit comparison characteristics. The primary berries tend to develop longitudinal creases and be irregularly wedge-shaped. The average soluble solid content of the fruit measured in percent Brix is 9.9, with percent Brix being an indirect measurement of the sugar content in fruit. The secondary and tertiary berries are typically much more uniformly cylindrical in shape with fewer longitudinal creases and irregular shapes. The fruit surface is medium red in coloration with a medium red colored flesh. The fruit coloration tends to be slightly uneven around the surface of the berry. The fruit surface is moderately to strongly uneven with the seeds typically held below the surface of the berry. The seed coloration varies from a moderately yellow color to a medium red with prolonged exposure to direct sunlight. Berries tend to develop seedy tips. Seedy tips may be so severe that a band of seeds may develop across the width of a wedge-shaped berry. A narrow band without achenes under the calyx is also common. The flesh is very firm, moderately glossy and moderately juicy, with a crunchy texture and good flavor. See Table 3 for fruit quality characteristics. The calyx is large in size, typically larger than the fruit diameter, with overlapping sepals. The pose of the calyx is almost never reflexed, (typically held flat to the berry). The calyx attaches firmly to the fruit and level with the surface of the berry. Fruit skin is considered only slightly susceptible to cracking due to rain.

Plant Characteristics

The plant of 'BG-424' is moderately vigorous, large in size with multiple crowns producing few runners when given the proper chilling levels prior to being dug, and artificially, prior to being planted. Excessive chilling will result in an over-vigorous, dense plant with a reduction in totol fruit yield and increased runner production. The plant is globose in character growing erect. The plant canopy becomes medium dense to dense when given proper chilling and cold storage. The average plant height for 'BG-424' is 12.9 cm, with a range of 10–16 cm, and the average plant spread is 25.3 cm, with a range of 22–30 cm.

Foliage Characteristics

'BG-424' foliage characteristics as compared to those of 'Camarosa'.

TABLE 4

Comparison of foliage characteristics of 'BG-424' and 'Camarosa' from Oxnard, California, April 19, 1999.

| Character | 'BG-424' | 'Camarosa' |
|---|---|---|
| Munsell Color (upper surface) | 7.5 GY 3/4 to 7.5 GY 3/6 | 5 GY 3/4 to 5 GY 3/6 |
| Terminal Leaflet Length | | |
| mean (cm) | 6.9 | 7.0 |
| range | 6.0–7.8 | 6.1–8.8 |
| Terminal Leaflet Width | | |
| mean (cm) | 6.5 | 6.6 |
| range | 5.8–7.8 | 6.0–7.7 |
| Terminal Leaflet ratio (L/W) | 1.05 | 1.06 |
| Petiole Length | | |
| mean (mm) | 15.3 | 12.7 |
| range | 12.2–17.3 | 7–15 |
| Petiole Width | | |
| mean (mm) | 3.2 | 2.8 |
| range | 2.6–4.0 | 2.1–3.2 |
| Petiolule Length | | |
| mean (mm) | 7.6 | 5.8 |
| range | 3–10 | 5–7 |
| Serrations/Leaf | | |
| mean | 19.8 | 17.5 |
| range | 18–23 | 15–21 |
| Serration Depth | | |
| mean (mm) | 5.4 | 5.0 |
| range | 4.5–6.9 | 4.6–5.9 |

The foliage of 'BG-424' has typically three leaflets per leaf, is medium in size, moderately glossy, medium green in color with medium to strong blistering. The terminal leaflet is greater in length than width as described by the length/width ratio, rounded in shape with an obtuse base. See Table 4 for foliage comparison characteristics. The leaf cross section of an immature terminal leaflet tends to be concave while a fully mature leaflet tends to be slightly concave to flat. Leaflets have many medium sized serrations. These serrations are rounded in shape, typically occur singly, occasionally in doubles. Petioles are considered long and moderate in thickness. Bract leaflets commonly occur singly or in pairs on petioles. Pubescence on the petioles is heavy, growing irregularly perpendicular to the petiole.

Flowers and Inflorescence

'BG-424' inflorescence and flower characteristics as compared to those of 'Camarosa'.

TABLE 5

Comparison of inflorescence characteristics of 'BG-424' and 'Camarosa' from Oxnard, California, May 29, 1999.

| Character | 'BG-424' | 'Camarosa' |
|---|---|---|
| Inflorescence Length | | |
| mean (cm) | 28.7 | 28.7 |
| range | 25–33 | 24–33 |
| Primary Peduncle Length | | |
| mean (cm) | 18.4 | 15.2 |
| range | 14–24 | 11–22 |
| Primary Peduncle Width | | |
| mean (mm) | 3.3 | 3.1 |
| range | 2.7–3.8 | 2.7–3.8 |
| Primary Pedicel Length | | |
| mean (cm) | 5.4 | 7.9 |
| range | 4.5–7.0 | 6.5–10.5 |
| Primary Pedicel Width | | |
| mean (mm) | 1.9 | 1.7 |
| range | 1.5–2.7 | 1.3–2.0 |

TABLE 6

Comparison of flower characteristics of 'BG-424' 'Camarosa' from Oxnard, California, April 15, 1999.

| Character | 'BG-424' | 'Camarosa' |
|---|---|---|
| Primary Calyx Diameter | | |
| mean (mm) | 43.7 | 44.9 |
| range | 38–48 | 37–53 |
| Primary Petal Length | | |
| mean (mm) | 14.6 | 12.8 |
| range | 12–17 | 11–14 |
| Primary Petal Width | | |
| mean (mm) | 13.4 | 12.3 |
| range | 11–16 | 11–14 |
| Primary Petal ratio (L/W) | 1.09 | 1.03 |
| Petals/Primary Flower | | |
| mean | 6.7 | 6.4 |
| range | 5–8 | 5–7 |
| Primary Sepal Length | | |
| mean (mm) | 17.5 | 18.3 |
| range | 13–21 | 15–22 |
| Primary Sepal Width | | |
| mean (mm) | 8.4 | 8.3 |
| range | 6–12 | 6–10 |
| Primary Sepal ratio (L/W) | 2.1 | 2.2 |
| Sepals/Primary Flower | | |
| mean | 13.3 | 12.7 |
| range | 11–16 | 10–15 |

The inflorescence of 'BG-424' are considered moderately long, almost never extending the fruit and flowers beyond the foliage. The average number of peduncles per 'BG-424' plant is 6.1, with a range of 3–9 per plant, and the average number of pedicels per 'BG-424' plant is 13.5, with a range of 6–24 per plant. The primary peduncle is typically non-existent during the early portion of the season then lengthens as the fruiting season progresses. The primary peduncle is considered medium in length and thickness late in the season. The pedicel holding the primary berry is considered short and typically originates singly from the apex of the primary peduncle or seldom from one of the secondary peduncles. Secondary and tertiary berries are borne on pedicels arising from secondary peduncle apex. The fruiting truss is typically prostrate at first picking. The average length of the fruiting truss is 28.7 cm, with a range of 25–33 cm. See Table 5 for inflorescence comparison characteristics. Flowers are large in size with overlapping petals averaging 5 to 8 large sized obovate petals per primary flower. The petals are longer than broad to much longer than broad as described by the length/width ratio and white in color. The corolla is typically smaller in relative comparison to the calyx. The average calyx diameter of 'BG-424' is 43.3 mm, with a range of 38–51 mm, and the average corolla diameter is 40 mm, with a range of 37–45 mm. See Table 6 for flower comparison characteristics. The average number of stamens per flower of 'BG-424' is 31.1, with a range of 28–41 per flower, and the average number of pistils per flower of 'BG-424' is 325, with a range of 225–430 per flower. Pollen is produced when the flower becomes fully open and the anthers mature. Medium anthocyanin coloration are present on the stolons, Munsell color rating near 2.5 YR 4/6–2.5 YR 5/6. Typically a medium to large bract leaf is borne on a petiole which originates at the primary peduncle apex alongside the base of one of the secondary peduncles. Bract leaves occur on nearly every inflorescence. The sepals are elliptical and narrow in shape.

Pest Reactions

This new variety may not be resistant to any of the known insects, diseases or viruses common in California. It is known to be moderately susceptible to the two-spotted spider mite, aphid and flower thrips. It is also known to be moderately susceptible to grey fruit mold, powdery mildew and highly susceptible to angular leafspot. The susceptibility of the new variety to any of the virus complexes of California has not been determined.

We claim:

1. A new and distinct variety of strawberry plant designated as 'BG-424', as herein described and illustrated by the characteristics set forth above.

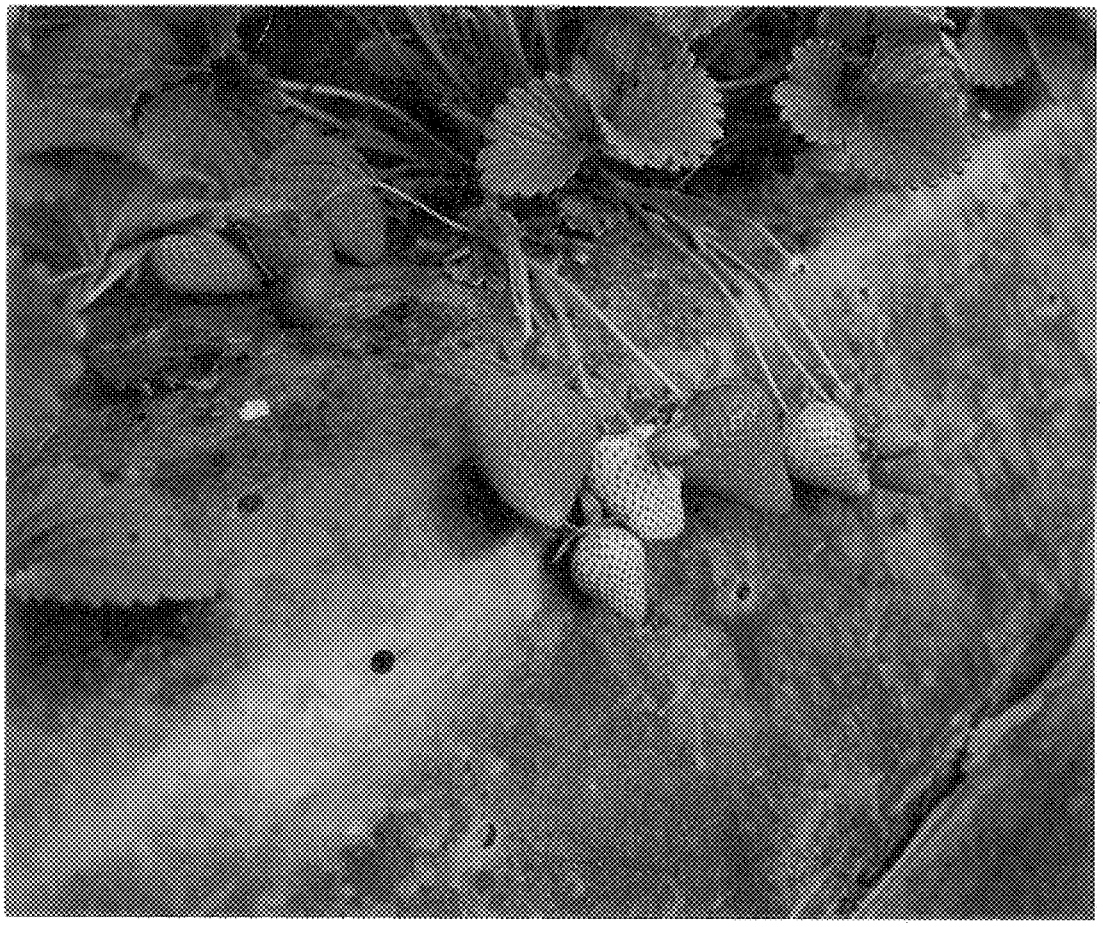

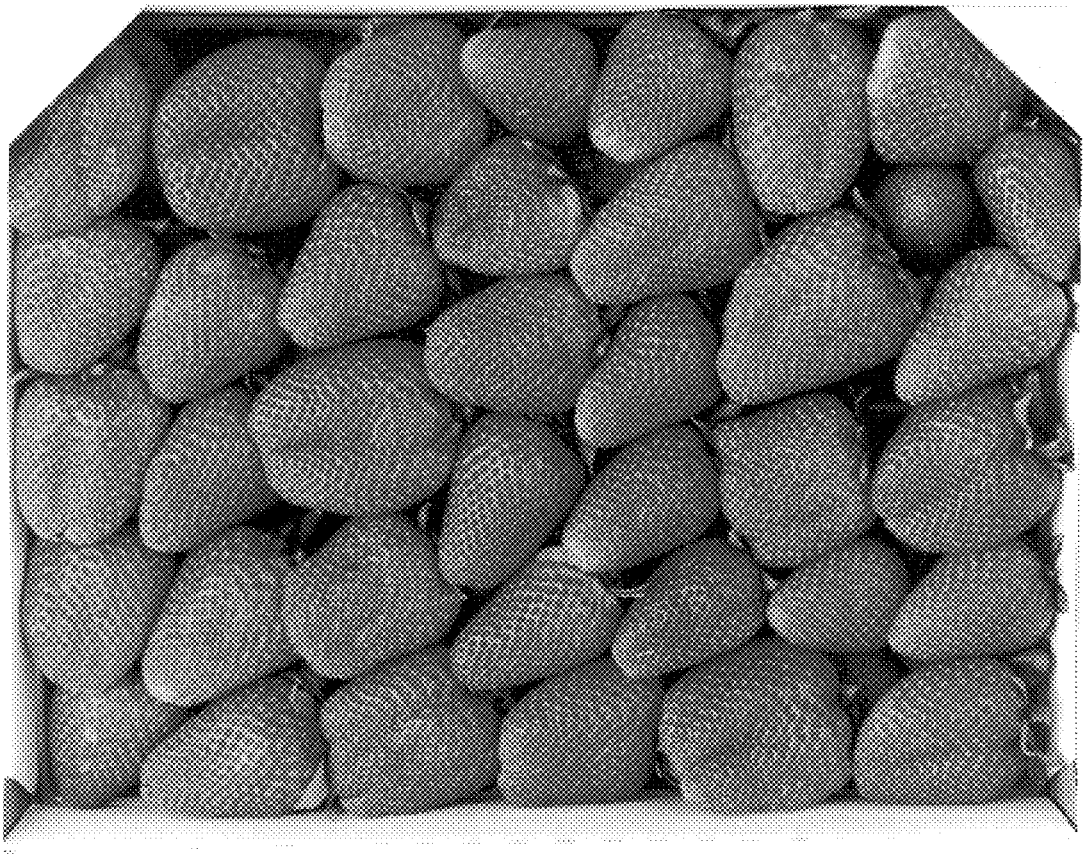

* * * * *